United States Patent [19]

Rokach et al.

[11] 4,091,105

[45] May 23, 1978

[54] 2-IMINO-3-AMINOTHIAZOLIDINES AND INDOLEAMINE-N-METHYLTRANSFERASE INHIBITION

[75] Inventors: Joshua Rokach, Laval, Canada; Clarence S. Rooney, Worcester, Pa.; Grant W. Reader, Montreal, Canada; Edward J. Cragoe, Jr., Lansdale, Pa.

[73] Assignee: Merck & Co., Inc., Rahway, N.J.

[21] Appl. No.: 823,909

[22] Filed: Aug. 12, 1977

Related U.S. Application Data

[63] Continuation of Ser. No. 696,244, Jun. 15, 1976, abandoned.

[51] Int. Cl.$^2$ .............. C07D 277/18; A61K 31/425
[52] U.S. Cl. ........................... 424/270; 260/306.7 T
[58] Field of Search ................. 424/270; 260/306.7 T

[56] References Cited

U.S. PATENT DOCUMENTS 3,471,510  10/1969  Benjamin ................ 260/306.7 T

Primary Examiner—R. J. Gallagher
Attorney, Agent, or Firm—Harry E. Westlake, Jr.; William H. Nicholson

[57] ABSTRACT

2-Imino-3-aminothiazolidines are inhibitors of indoleamine-N-methyl transferase in vivo.

3 Claims, No Drawings

2-IMINO-3-AMINOTHIAZOLIDINES AND INDOLEAMINE-N-METHYLTRANSFERASE INHIBITION

This is a continuation, of application Ser. No. 696,244 filed June 15, 1976, now abandoned.

BACKGROUND OF THE INVENTION

This invention is concerned with 2-imino-3-aminothiazolidine and derivatives thereof which by virtue of their ability to inhibit indoleamine-N-methyl transferase are useful in the treatment of certain mental aberrations in man, such as schizophrenia.

This invention also relates to processes for the preparation of the imines of this invention; to pharmaceutical compositions comprising the imines; and to a method of treating mental aberrations, such as schizophrenia, comprising the administration of the imines and compositions thereof. The imines may be depicted by the generic structure:

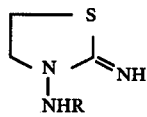

wherein R is hydrogen, methyl, or ethyl.

N,N-dimethylindoleamines such as dimethylserotonin and dimethyltryptamine are psychotomimetic agents and are believed to be produced in excessive amounts by individuals with certain mental aberrations, most commonly classified as schizophrenia. Indoleamine-N-methyl transferase is an enzyme which catalyzes the methylation steps in the biosynthesis of these compounds. Accordingly, it is believed by those skilled in the art that inhibitors of this enzyme will be of therapeutic value in management of the body chemistry of patients having mental aberrations such as schizophrenia and thus result in alleviating some of the symptoms of the disease. Thus it is an object of the present invention to provide the above-described imines and their pharmaceutically acceptable acid addition salts; to provide processes for the preparation of such compounds; pharmaceutical compositions comprising such compounds; and to provide methods of treatment comprising administering such compounds and compositions, when indicated for the treatment/management of mental aberrations such as schizophrenia.

DETAILED DESCRIPTION OF THE INVENTION

The novel compounds of this invention have structural formula I:

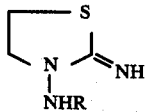

or pharmaceutically acceptable salt thereof, wherein R represents hydrogen, methyl, or ethyl.

The pharmaceutically acceptable salts of this invention are acid addition salts prepared from mineral or organic acids commonly employed in the pharmaceutical art, such as hydrobromic, hydrochloric, fumaric, ethane disulfonic, or the like.

In the novel method of treatment of this invention the route of administration can be oral, rectal, intravenous, intramuscular, or intraperitoneal. Doses of 0.10 to 100 mg./kg./day and preferably of 1 to 10 mg./kg./day of active ingredient are generally adequate, and it is preferred that it be administered in divided doses given two to four times daily.

It is to be noted that the precise unit dosage form and dosage level depend upon the case history of the individual being treated and, consequently, are left to the discretion of a skilled therapist.

Pharmaceutical compositions comprising a compound useful in the novel method of treatment as active ingredient may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and intraperitoneal use the pharmaceutical compositions may be in any art recognized form of a sterile injectable preparation such as sterile aqueous or oleaginous solution or suspension. The amount of active ingredient incorporated in a unit dosage of the above described pharmaceutical compositions may be from 1 mg. to 500 mg.

The compounds of this invention are prepared by the following process:

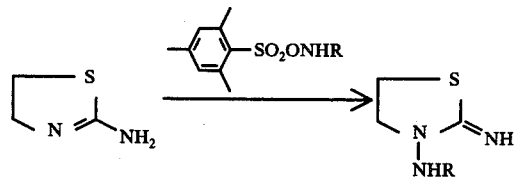

wherein R is hydrogen, methyl, or ethyl.

The process comprises mixing 2-aminothiazoline with a mesitylenesulfonylhydroxylamine in a solvent such as chloroform, methylene chloride, tetrachloroethane or the like at −10° to +10° C. followed by 1–6 hours at 15°–30° C.

The starting materials for the novel process of this invention and processes for preparing them as well as the preparation of the novel compounds of this invention are fully described in the Examples that follow.

EXAMPLE 1

2-Imino-3-methylaminothiazolidine and Maleate Salt

Step A: Preparation of N-t-butoxycarbonyl-N-methyl hydroxylamine

N-methylhydroxylamine hydrochloride (14.6 g.) in 20 ml. of water was cooled in an ice-bath and treated with 20 g. of t-butyl azidoformate. A solution of 22.4 g. of sodium hydroxide in 80 ml. of water was added dropwise with stirring over 45 minutes while controlling the temperature below 10° C. The mixture was allowed to warm to room temperature with stirring over a 60 minute period after the addition during which time a little more sodium hydroxide solution and N-methyl hydroxylamine were added. The solution was extracted with 2 × 50 ml. of ether, and the extracts were discarded. The aqueous phase, with cooling, was adjusted to pH 3.5 with 6 N hydrochloric acid, and extracted with 5 × 60 ml. of ether. The combined ether extracts were dried over magnesium sulfate and evaporated to 16 g. of oily N-t-butoxycarbonyl-N-methyl hydroxylamine.

Step B: Preparation of N-t-butoxycarbonyl-N-methyl mesitylenesulfonylhydroxylamine A solution of 16 g. of N-t-butoxycarbonyl-N-methyl hydroxylamine and 23.8 g. of mesitylenesulfonyl chloride in 400 ml. of ether was cooled to 0° C. and treated with 15.4 ml. of triethylamine dropwise with stirring. Thirty minutes after the addition was complete, the mixture was filtered, and the filter cake was washed with 2 portions of ether. The filtrate and washings were evaporated to a heavy oil. The oil was dissolved in 40 ml. of benzene, filtered through diatomaceous earth and concentrated to dryness to give a crystalline residue of N-t-butoxycarbonyl-N-methyl mesitylenesulfonylhydroxylamine, which was used directly in the next step without characterization.

Step C: Preparation of N-methyl mesitylenesulfonylhydroxylamine

N-t-butoxycarbonyl-N-methyl mesitylenesulfonylhydroxylamine, 4 g., was added to 15 ml. of trifluoroacetic acid in an ice bath and stirred until solution was complete. The solution was poured onto 100 ml. ice/water. The precipitate was collected, air dried for about 15 minutes, dissolved in 10 ml. of ether, treated with 50 ml. of petroleum ether (30°–60° C.) and cooled in an ice bath for 15 minutes. The precipitate was collected and air dried to give 2 g. (75%) of N-methyl mesitylenesulfonylhydroxylamine, m.p. 83°–84° C.

Step D: Preparation of 2-imino-3-methylaminothiazolidine and maleate salt

A solution of 0.47 g. of 2-aminothiazoline in 4 ml. of methylene chloride was added to a solution of 1 g. of N-methyl mesitylenesulfonylhydroxylamine in 4 ml. of methylene chloride with cooling in an ice-bath. The mixture was allowed to warm to, and was stirred at, ambient temperature for 3 hours. Ether (50 ml.) was added. The solvent was decanted and the precipitate was dissolved in 5–10 ml. of methanol and precipitated with ether. The crystalline precipitate was collected, washed with ether and air dried to give 0.9 g. of 2-imino-3-methylaminothiazolidine mesityl sulfonic acid salt, m.p. 115°–118° C.

The free base was converted to the maleate salt by treatment with the calculated quantity of maleic acid in isopropanol and adding ether to precipitate the maleate salt, m.p. 93°–95° C.

Employing the procedure substantially as described in Example 1, Steps A through D, but substituting for the N-methyl hydroxylamine hydrochloride used in Step A thereof, an equimolecular amount of N-ethyl hydroxylamine hydrochloride, there is produced 2-imino-3-ethylaminothiazolidine maleate salt.

Employing the procedure of Example 1, Step D, but substituting for the N-methyl mesitylenesulfonylhydroxylamine used therein, an equimolecular amount of mesitylenesulfonylhydroxylamine, there is produced 2-imino-3-aminothiazolidine maleate salt, m.p. 122°–123° C.

EXAMPLE 2

Pharmaceutical Compositions

A typical tablet containing 5 mg. of 2-imino-3-aminothiazolidine per tablet is prepared by mixing together with the active ingredient calcium phosphate, lactose and starch in the amounts shown in the table below. After these ingredients are thoroughly mixed, the dry mixture is blended for an additional three minutes. This mixture is then compressed into tablets weighing approximately 129 mg. each. Similarly prepared are tablets containing 3-ethylamino-2-imino-thiazolidine maleate or 2-imino-3-methylaminothiazolidine maleate.

| Tablet Formula | |
|---|---|
| Ingredient | Mg. per tablet |
| Active Ingredient | 5 mg. |
| Calcium phosphate | 52 mg. |
| Lactose | 60 mg. |
| Starch | 10 mg. |
| Magnesium stearate | 1 mg. |

What is claimed is:

1. A compound of structural formula:

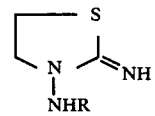

or pharmaceutically acceptable salt thereof, wherein R is hydrogen, methyl, or ethyl.

2. A method of inhibiting indoleamine-N-methyltransferase which comprises administering to a patient in need of such treatment an amount effective to inhibit indoleamine-N-methyltransferase of a compound of structural formula:

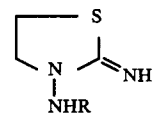

or pharmaceutically acceptable salt thereof, wherein R is hydrogen, methyl, or ethyl.

3. A pharmaceutical composition comprising a pharmaceutical carrier and an amount effective to inhibit indoleamine-N-methyltransferase of a compound of structural formula:

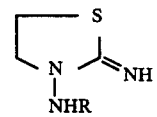

or pharmaceutically acceptable salt thereof, wherein R is hydrogen, methyl, or ethyl.

* * * * *